United States Patent
Sun et al.

(10) Patent No.: US 6,399,143 B1
(45) Date of Patent: *Jun. 4, 2002

(54) METHOD FOR CLAMPING AND ELECTROSTATICALLY COATING A SUBSTRATE

(75) Inventors: Hoi Cheong Steve Sun, Monmouth Junction; Bogdan Brycki, Mt. Laurel, both of NJ (US)

(73) Assignee: Delsys Pharmaceutical Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/095,321

(22) Filed: Jun. 10, 1998

Related U.S. Application Data

(63) Continuation-in-part of application No. 08/630,012, filed on Apr. 9, 1996, now Pat. No. 5,788,814.

(51) Int. Cl.[7] .................................................. A61J 3/00
(52) U.S. Cl. ...................... 427/2.14; 427/2.31; 427/466; 427/475; 427/483
(58) Field of Search .............................. 427/2.14, 2.19, 427/2.31, 8, 458, 459, 466, 475, 483

(56) References Cited

U.S. PATENT DOCUMENTS

| | | | |
|---|---|---|---|
| 4,551,192 A | 11/1985 | Di Milia et al. ............ 156/345 |
| 4,640,846 A | 2/1987 | Kno ............................ 427/82 |
| 4,652,318 A | * 3/1987 | Masuda et al. |
| 4,718,681 A | 1/1988 | Kakehi et al. .............. 279/106 |
| 5,042,421 A | 8/1991 | Anbe .......................... 118/52 |
| 5,155,652 A | * 10/1992 | Logan et al. |
| 5,234,499 A | 8/1993 | Sasaki et al. ................. 118/52 |
| 5,532,903 A | * 7/1996 | Kendall |
| 5,548,470 A | 8/1996 | Husain et al. .............. 361/234 |
| 5,624,499 A | 4/1997 | Mizuno et al. ............. 118/725 |
| 5,675,471 A | 10/1997 | Kotecki ...................... 361/234 |
| 5,676,758 A | 10/1997 | Hasegawa et al. .......... 118/173 |
| 5,692,873 A | 12/1997 | Weeks et al. ............... 414/627 |
| 5,723,367 A | 3/1998 | Wada et al. ................. 437/248 |
| 5,724,121 A | 3/1998 | McKinley et al. ........... 355/53 |
| 5,788,814 A | * 8/1998 | Sun et al. |

FOREIGN PATENT DOCUMENTS

| | | | |
|---|---|---|---|
| GB | 2 149 697 | * | 6/1985 |
| WO | WO 97/37803 | | 10/1997 |

* cited by examiner

Primary Examiner—Fred J. Parker
(74) Attorney, Agent, or Firm—Dechert

(57) ABSTRACT

The disclosure relates to an apparatus for electrostatically adhering grains to a planar substrate comprising:

a. an electrostatic chuck having a collection surface with at least one grain collection zone for, when the planar substrate is layered on the collection surface, electrostatically directing charged grains to a corresponding surface on the planar substrate; and b. a pattern of holes through the electrostatic chuck allowing a source of low pressure to act through the electrostatic chuck to adhere the planar substrate.

6 Claims, 9 Drawing Sheets

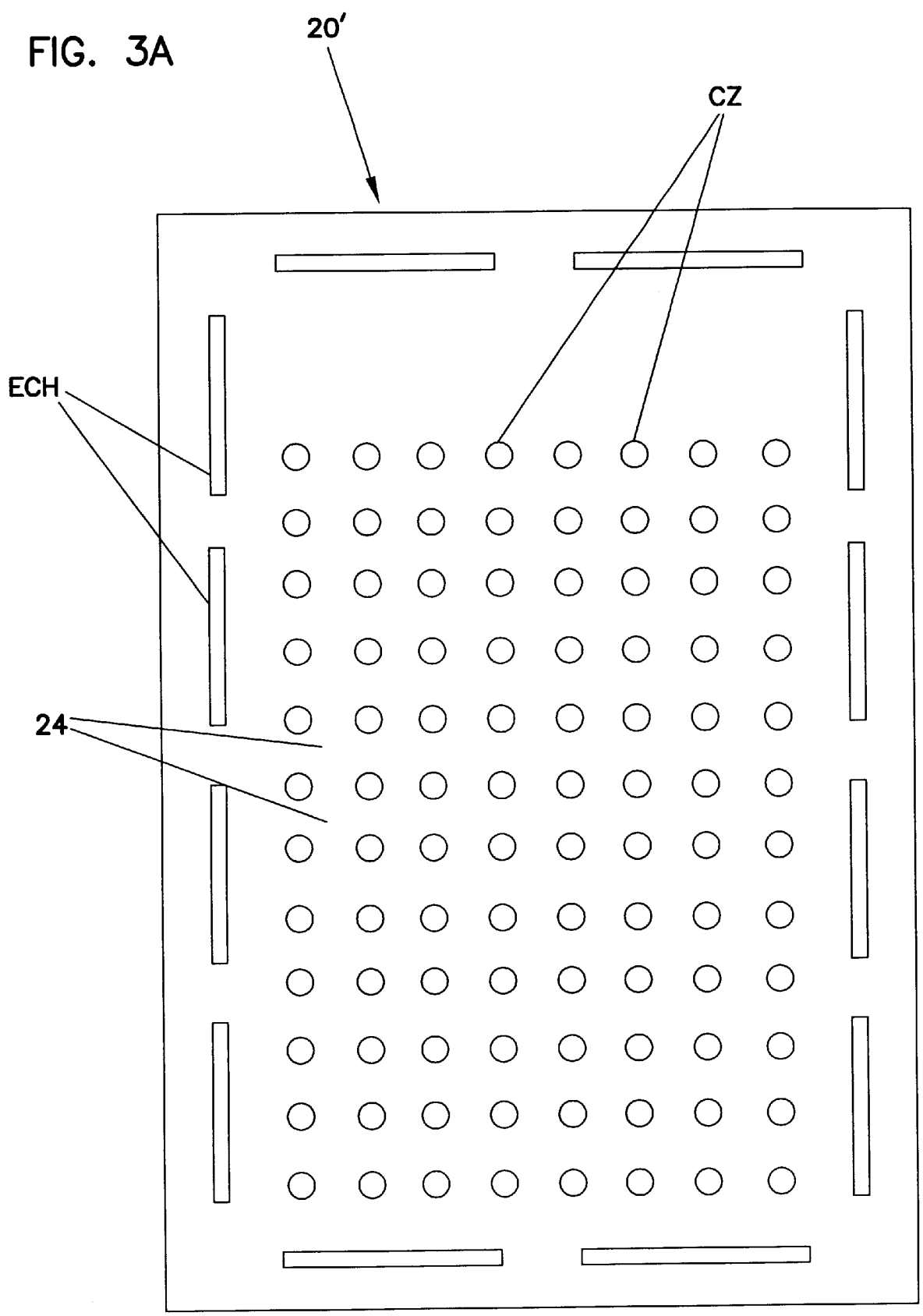

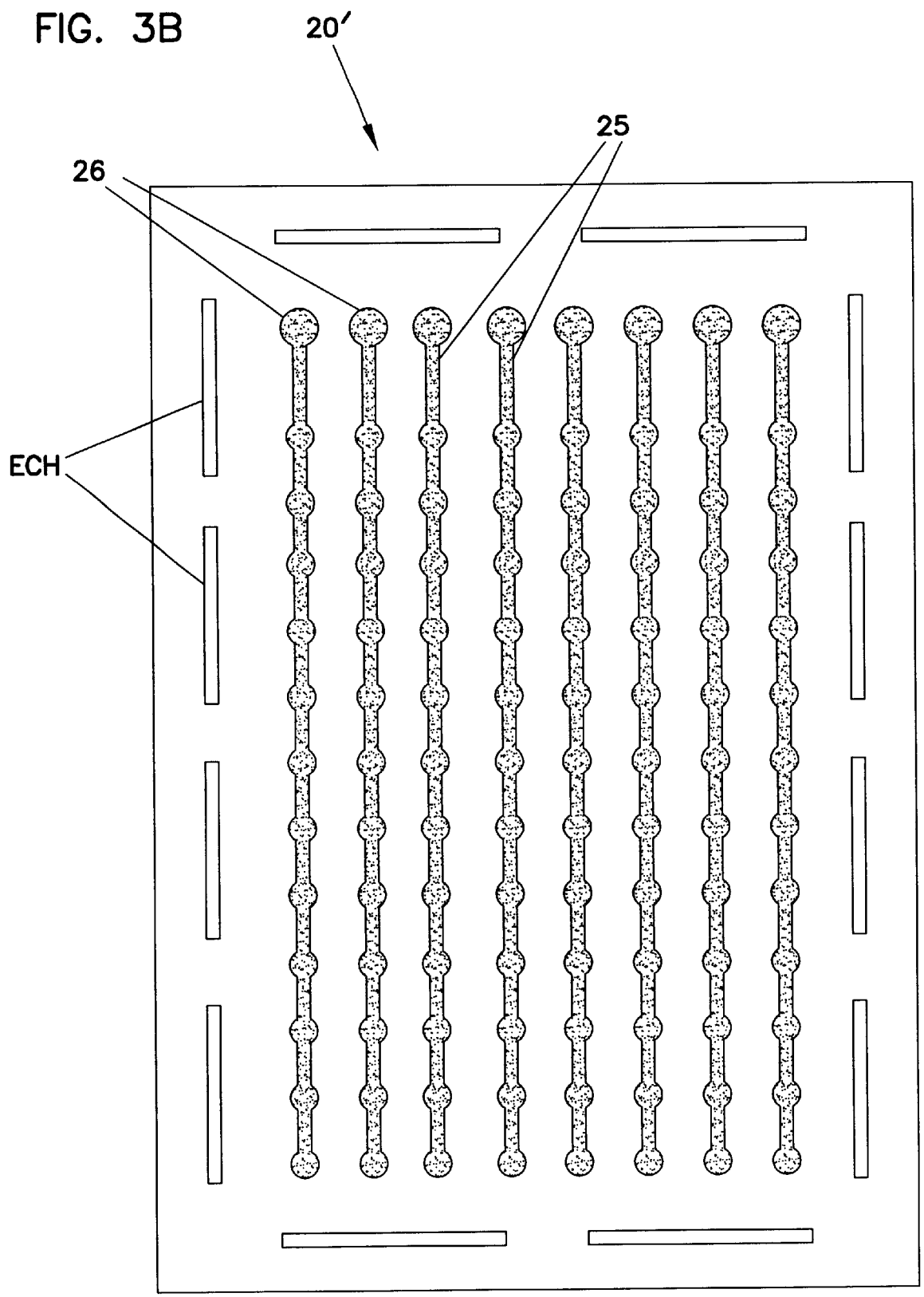

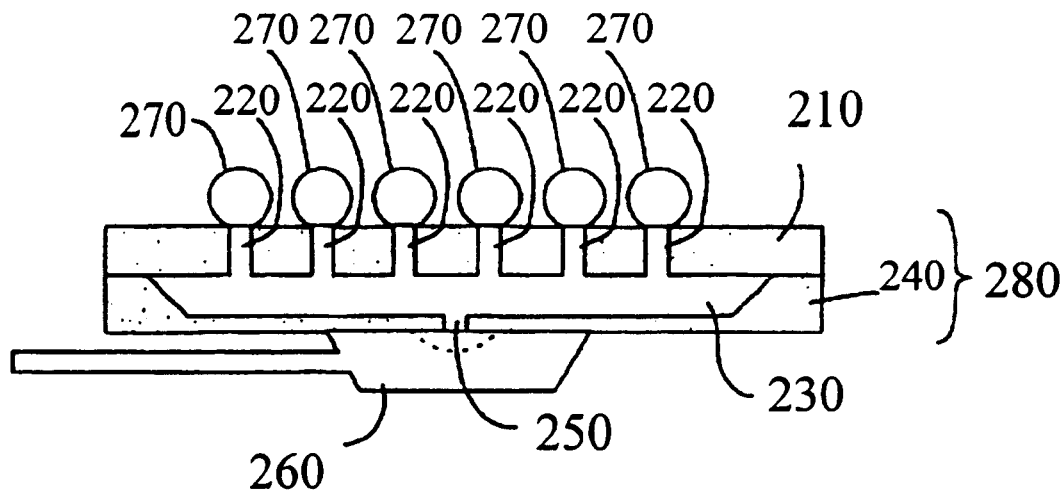
FIG. 9
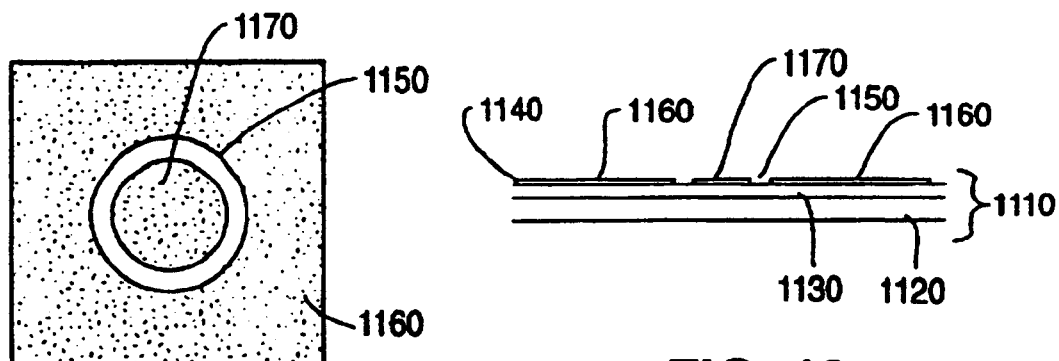
FIG. 11
FIG. 10

METHOD FOR CLAMPING AND ELECTROSTATICALLY COATING A SUBSTRATE

The present application is a Continuation-in-part of U.S. application Ser. No. 08/630,012, filed Apr. 9, 1996, now U.S. Pat. No. 5,788,814.

The present invention relates to a apparatus and method for using a vacuum chuck to assure adhesion of a planar substrate, while using electrodes to attract grains (e.g., dry powder) to adhere to the planar substrate. The electrodes may also participate in holding the planar substrate.

In the field of semiconductor processing, semiconductor wafers have been held in place for processing with clamps, magnetic clamps, electrostatic chucks and vacuum chucks. Such semiconductor processing typically seeks to direct mask material, mask developing materials such as photoresist, dopant and etchant to the semiconductor. In directing etchant to the semiconductor, electromagnetic fields may be used to direct the majority of etching to occur in a given direction; such directed etching processes were not intended to coat the semiconductor with grains. For example, Weeks et al., U.S. Pat. No. 5,692,873, McKinley et al., U.S. Pat. No. 5,724,121 and Hasegawa et al., U.S. Pat. No. 5,676,758 all describe vacuum chucks in connection with various semiconductor apparatuses, and also mention that electrostatic chucks can also be used to clamp the semiconductor wafer. A Di Milia et al. patent, U.S. Pat. No. 4,551,192, describes a pinchuck that can be used to hold a substrate during a lithography process using vacuum or electrostatic forces.

Electrostatic chucks can be used to direct grains of material to a substrate to provide a coated substrate. Various methods can be used to assure that such coating techniques apply an accurate and, in some cases, spatially resolved, coating of material, making it feasible to use electrostatic coating technology to apply pharmaceuticals. "Spatially resolved" refers to depositions at defined subregions of a surface. Examples of technology in this area include Sun, "Chucks and Methods for Positioning Multiple Objects on a Substrate," U.S. Pat. No. 5,788,814, issued Aug. 4, 1998; Sun et al., "Electrostatic Chucks," U.S. Pat. No. 5,858,099, issued Jan. 12, 1999; Pletcher et al., "Method and Apparatus for Electrostatically Depositing a Medicament Powder Upon Predefined Regions of a Substrate," U.S. Pat. No. 6,007,630, issued Dec. 28, 1999; and Sun et al., "Acoustic Dispenser," U.S. Pat. No. 5,753,302, issued May 19, 1998. These documents are incorporated by reference herein in their entirety.

In the course of testing such accurate deposition apparatuses to coat flexible planar substrates, applicant has discovered that while the electrostatic chuck can be used to hold the planar substrate and direct the electrostatic deposition of grains, a combination further using vacuum forces on the chuck increases the processing efficiency such that the planar substrate more reproducibly becomes adhered without deformations and air pockets. Such a combination preferably takes the form of a vacuum chuck onto which is layered a thin, e.g., about 25 µm to about 250 µm thick electrostatic chuck having holes through which the vacuum is communicated to the planar substrate.

Summary of the Invention

In one embodiment, the invention relates to an apparatus for electrostatically adhering grains to a planar substrate comprising:

a. an electrostatic chuck having a collection surface with at least one grain collection zone for, when the planar substrate is layered on the collection surface, electrostatically directing charged grains to a corresponding surface on the planar substrate; and b. a pattern of holes through the electrostatic chuck allowing a source of low pressure to act through the electrostatic chuck to adhere the planar substrate.

The apparatus can further comprise:

c. a low pressure chuck having an adhesion surface having a plurality of holes for aligning with the holes to connect the holes to the source of low pressure.

The adhesion surface can be a porous material.

In one embodiment, the electrostatic chuck comprises (i) the collection surface, (ii) a dielectric layer located behind the collection surface, (iii), behind the dielectric layer, one or more attraction electrodes for attracting grains to the collection zones. Also, the electrostatic chuck can further comprises (iv) one or more shield electrodes for discouraging charged grains from being directed away from the collection zones. A rotatable cluster of a plurality of said low pressure chucks can be used, where the low pressure chucks rotate to repeatedly and sequentially present the adhesion surfaces to the charged grain dispenser. A low pressure control mechanism can be operated to sequentially apply low pressure to low pressure chucks and sequentially releasing the low pressure from low pressure chucks such that there is a contiguous collection of the low pressure chucks to which low pressure is applied and a contiguous collection of the low pressure chucks with no applied low pressure, thereby allowing a sheet of planar substrate to be presented to the charged grain dispenser while adhered to an electrostatic chuck and low pressure chuck and then released for further processing.

Also provided is an electrostatic deposition apparatus for electrostatically depositing grains onto a planar substrate comprising:

i. at least one low pressure chuck having an adhesion surface having a plurality of holes for conveying low pressure to the adhesion surface;

ii. layered on the collection surface, at least one electrostatic chuck having a collection surface with at least one grain collection zone for, when the planar substrate is layered on the collection surface, electrostatically directing charged grains to a corresponding surface on the planar substrate, the at least one electrostatic chuck having a pattern of holes through the electrostatic chuck allowing the low pressure to act through the electrostatic chuck to adhere the planar substrate; and iii. a charged grain dispenser for directing charged grains towards the grain collection zones.

Still further provided is a method of electrostatically applying a grains to a planar substrate comprising:

a. adhering the planar substrate to an electrostatic chuck with a pressure differential conveyed to the planar substrate via passages through the electrostatic chuck;

b. applying a voltage to the electrostatic chuck to attract charged grains to at least one grain collection zone defined by the electrostatic chuck;

c. directing charged grains towards the charged grain collection zone; and d. electrostatically adhering charged grains on a portion of the planar substrate corresponding to the grain collection zone.

BRIEF DESCRIPTION OF THE DRAWINGS

FIG. 3A shows the upper surface of another electrostatic chuck.

FIG. 3B shows a rear surface of the electrostatic chuck.

FIG. 9 shows an exemplary vacuum chuck.

FIG. 10 is a cross-sectional schematic view of an electrostatic chuck with floating electrodes on the upper conductive layer for charge imaging.

FIG. 11 is a top view of a floating electrode of FIG. 10.

DEFINITIONS

The following terms shall have, for the purposes of this application, the respective meaning set forth below.

delivery to an animal: A delivery device for delivering defined amounts of reagents to an animal delivers such defined amounts to a tissue of the animal. For example, the device can deliver reagents orally, sublingually, rectally, nasally, vaginally, topically (including the use of a patch or other transdermal delivery device), by pulmonary route (for instance by use of an aerosol or powder cloud), or parenterally (including, for example, intramuscularly, subcutaneously, intraperitoneally, intraarterially, intravenously or intrathecally).

dry deposited: A material is "dry deposited" if deposited without applying the material in a liquid vehicle.

excipient: Excipients are pharmaceutically acceptable organic or inorganic carrier substances suitable for parenteral, enteral (e.g., oral or inhalation) or topical application. Preferably, these excipient do not react deleteriously with the active compositions. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxymethylcellulose, polyvinylpyrrolidinone, and the like.

effective amount: The meaning of "effective amount" will be recognized by clinicians but includes amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease, or the symptoms thereof.

electro-attractive dry deposition: This term refers to methods that use an electromagnetic field, or an electrostatically charged surface to dry deposit charged grains (e.g., particles).

grains are, for the purposes of this application, either aggregates of molecules or particles, preferably of at least about 3 nm average diameter, preferably at least about 500 nm or 800 nm average diameter. Grains are, for example, particles of a powder such as a dry powder.

planar substrate is intended to denote a substrate which is predominately formed with two major dimensions, such as a tape or sheet. The term does not imply that the substrate is flat.

DETAILED DESCRIPTION OF THE INVENTION

Combined Electrostatic and Vacuum Clucks

Figure 1A:
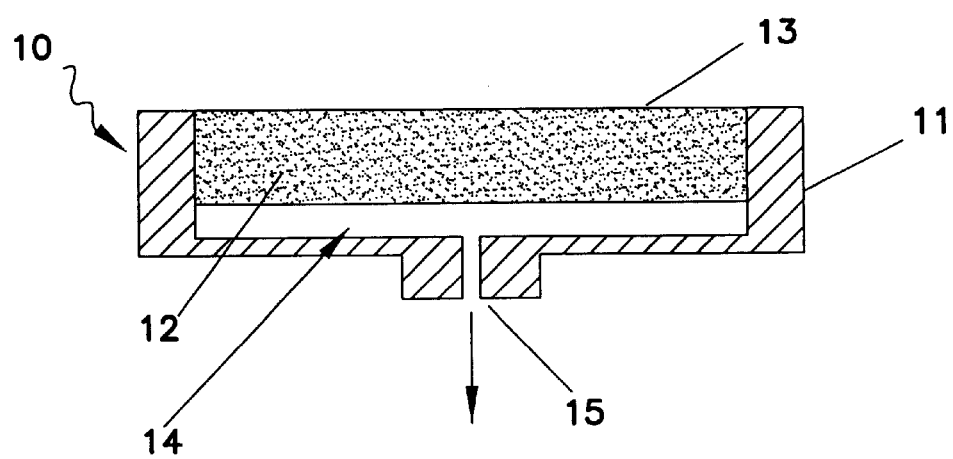
FIG. 1A illustrates a vacuum chuck used with the apparatus for electrostatically adhering grains of the present invention.
Figure 1B:
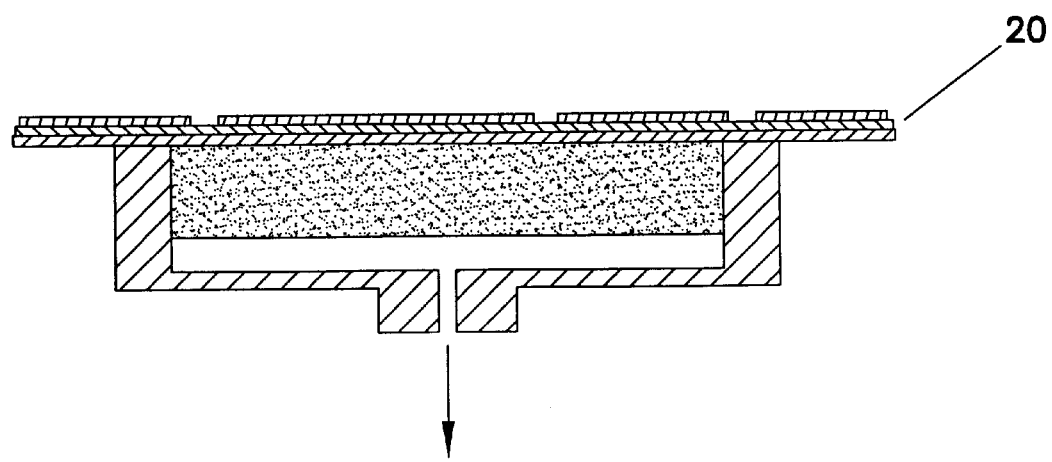
FIG. 1B shows an electrostatic chuck adhered to an adhesion surface of the vacuum chuck.

FIG. 1A illustrates a vacuum chuck used with the apparatus for electrostatically adhering grains of the present invention. The vacuum chuck 10 is made up of a porous disk 11, on which is mounted a porous material 12, such as a sintered material such as a sintered ceramic. The upper surface of the porous material is an adhesion surface 13. Beneath the adhesion surface 13 is a vacuum chuck manifold 14, which connects to a source of low pressure via outlet 15. FIG. 1B shows an electrostatic chuck 20 made up of three layers (described further below) adhered to the adhesion surface. It should be noted that all references to relative orientation such as "upper," "beneath" and the like are made to facilitate describing the invention with reference to the exemplary drawings, and are not intended to limit the invention.

The illustrated vacuum chuck 10 has a porous disk 11, which can be for example a porous metal such as aluminum or steel, a sintered ceramic, or a sintered glass. The average pores of the disk can be, for example, from out 20 $\mu$m to about 500 $\mu$m, such as about 20 $\mu$m. The vacuum transmitting surface can also be, for example, a surface in which a series of holes have been formed.

Figure 2A:
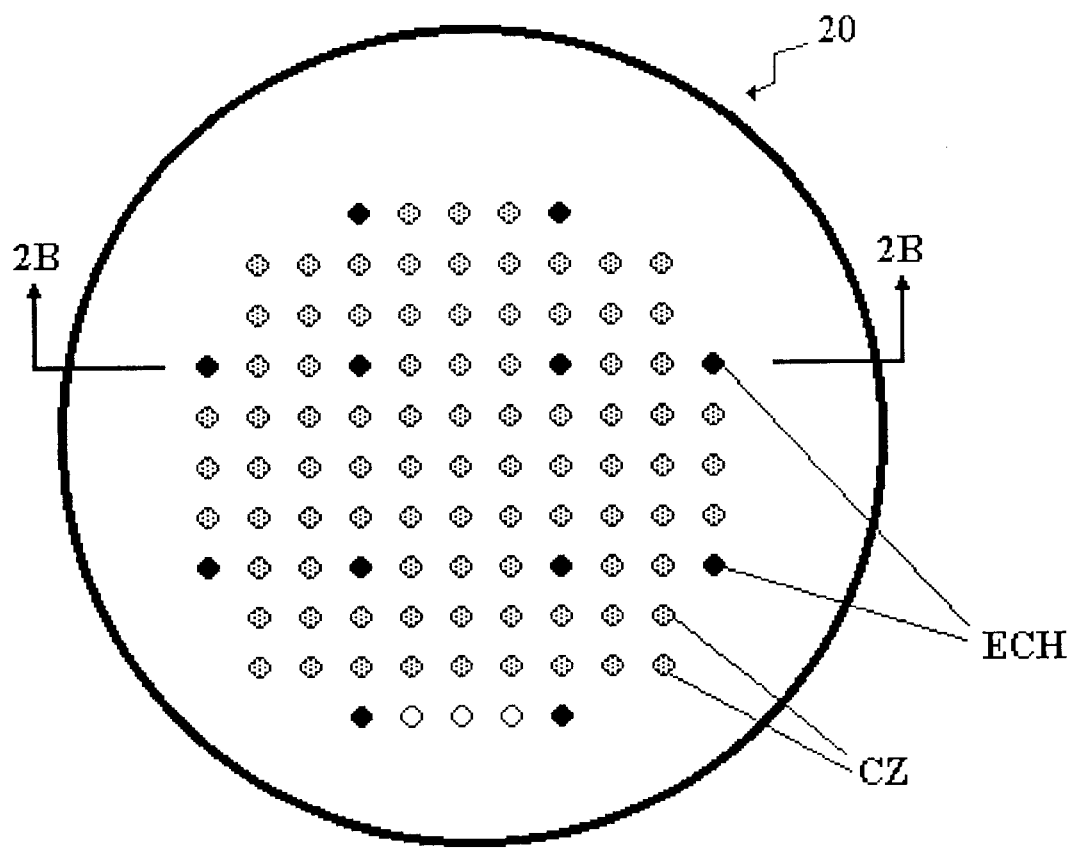
FIG. 2A shows the upper surface of a three-layer electrostatic chuck.
Figure 2B:
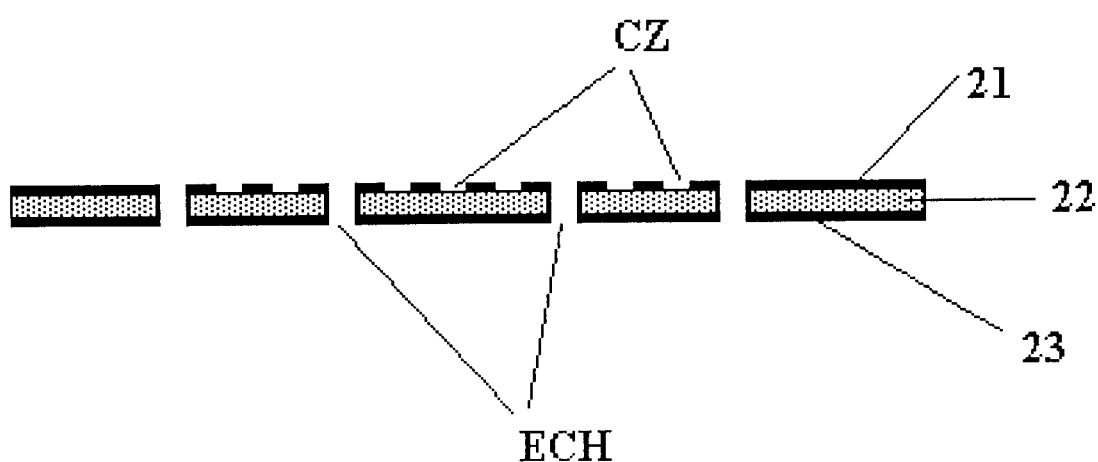
FIG. 2B shows the cross-section indicated in FIG. 2A.

FIG. 2A shows the upper surface of a three-layer electrostatic chuck 20. FIG. 2B shows the cross-section indicated in FIG. 2A. The electrostatic chuck has through holes ECH that allow the vacuum from a vacuum chuck such as vacuum chuck 10 to be conveyed through the electrostatic chuck 20 to the planar substrate. While in many embodiments the electrostatic chuck is adhered to the vacuum chuck by, for example, a clamp or adhesive, the vacuum can assure that the electrostatic chuck, which can be quite thin and flexible, is conformed to an appropriate shape. The electrostatic chuck 20 is made up of a shield electrode 21, a dielectric layer 22 and a grain-attracting electrode 23. Openings in the shield electrode 21 define collection zones CZ. Openings through the electrostatic chuck define the through holes ECH. The grains attracted are typically appropriately charged as described below and in the documents described therein. An appropriate potential, such as without limitation about 200 V to about 2,500 V or to about 3,000 V of a given polarity is applied to the grain-attracting electrode 23, while a ground potential or an opposite potential is applied to the shield electrode 21. (As indicated in copending U.S. Pat. No. 6,149,774, issued Nov. 21, 2000, "AC Waveforms Biasing for Bead Manipulating Chucks," the grain-attracting voltage can be applied in a pulsatile manner, allowing better results in attracting grains to conductive substrates.)

The illustration is not to scale. Electrostatic chucks that have been used with the invention have been, for example, about 10 cm in diameter, or about 10 by 15 cm. The thickness of the shield electrode is, for example, about 0.1 $\mu$m to about 50 $\mu$m, or about 10 $\mu$m to about 25 $\mu$m. The thickness of the dielectric layer is, for example, about 10 $\mu$m to about 75 $\mu$m, or about 15 $\mu$m to about 25 $\mu$m. The thickness of the grain-attracting electrode is, for example, about 0.1 μm to about 50 μm, or about 15 μm to about 25 μm. These thicknesses are selected to assure that the bead-attracting electrode can create a sufficient field to attract grains to regions of the planar substrate located above the collection zones CZ. Additionally, the thickness of the dielectric layer 22 and the planar substrate can be selected so that, once deposited on the planar substrate, the charged grains cause charge redistributions in the grain-attracting electrode that create an image force that can be larger than that due to the voltage applied to the grain-attracting electrode.

In one embodiment, the grain-attracting electrode 23 can be fabricated by depositing, using known techniques, such as using a 5000 Angstrom layer of gold (Au) onto the dielectric layer 22. Alternatively, grain-attracting electrode 23 can comprise, for example, a 100 Angstrom layer of chromium (Cr) and with a 5000 Angstrom gold (Au) overcoat. Dielectric layer 22 can be made of, for example, Dupont® Kapton® polyimide film (type 300 HN, for example, 3 mil thickness, from Dupont DeNemours, Willmington, Del.) or on Corning Pyrex 7740 glass, for example of 10 mils thickness (Corning Glass, Corning, N.Y.). Shield electrode 21 can comprise, for example, a 35 micron deposition of copper (Cu) onto the dielectric layer 22.

Figure 3C:
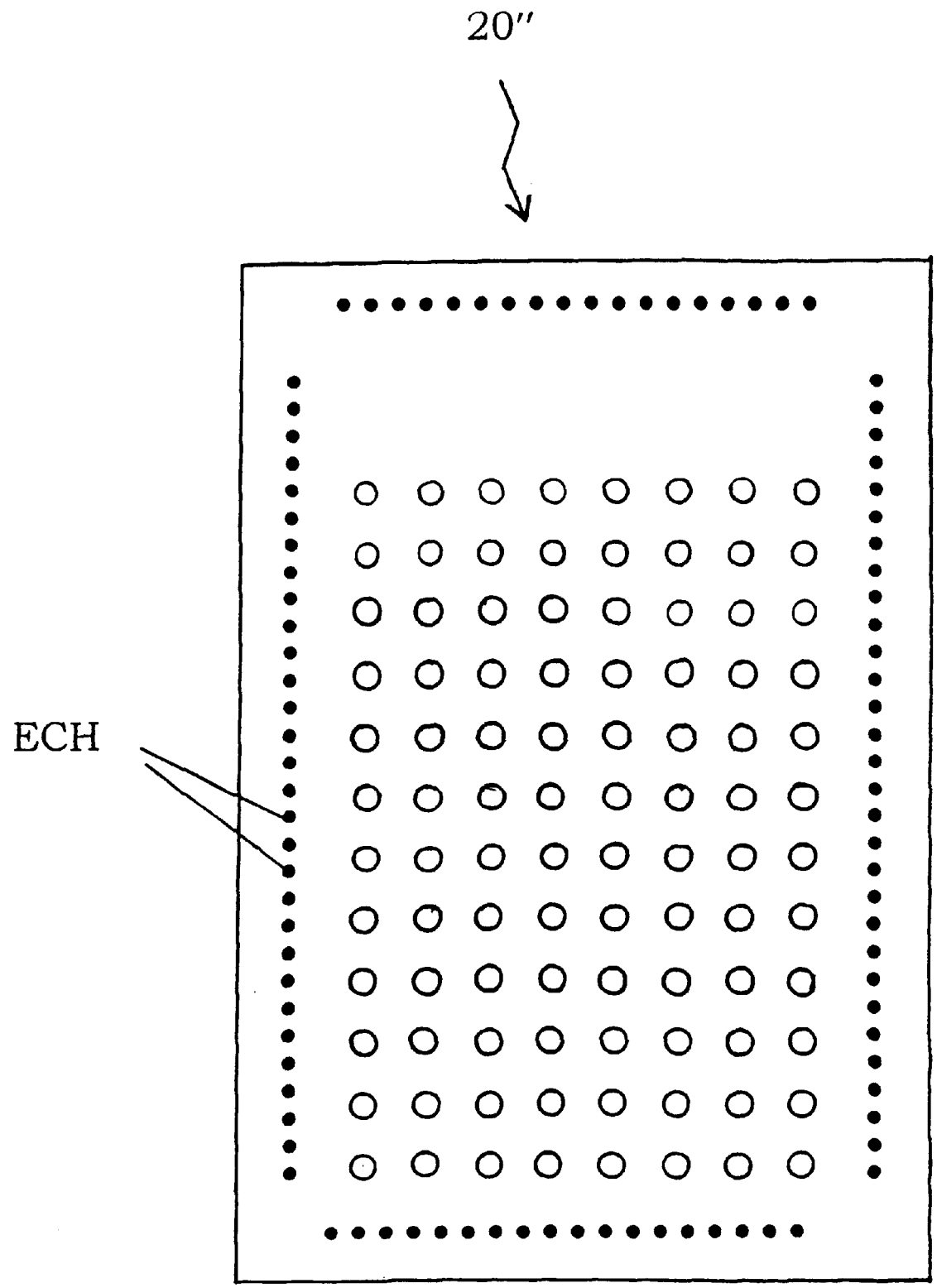
FIG. 3C shows an alternative embodiment where the through holes are rounded holes instead of slots.

FIG. 3A shows the upper surface of electrostatic chuck 20', which differs from electrostatic chuck 20 by having electrostatic chuck through holes ECH that are slots and located on the periphery;;of the electrostatic chuck 20'. The collection zones CZ are located on a surface 24 otherwise composed of a dielectric material. The through holes ECH are less susceptible to blockage by dust and other particles. FIG. 3B shows a rear surface of the electrostatic chuck 20', which has addressing electrodes 25 through which each row of the electrodes forming the collection zones CZ can be connected to driving electronics. Electrical contact pads 26 provide contact points for connections to voltage sources. FIG. 3C shows an alternative embodiment where the through holes ECH are rounded holes instead of slots.

Figure 4A:
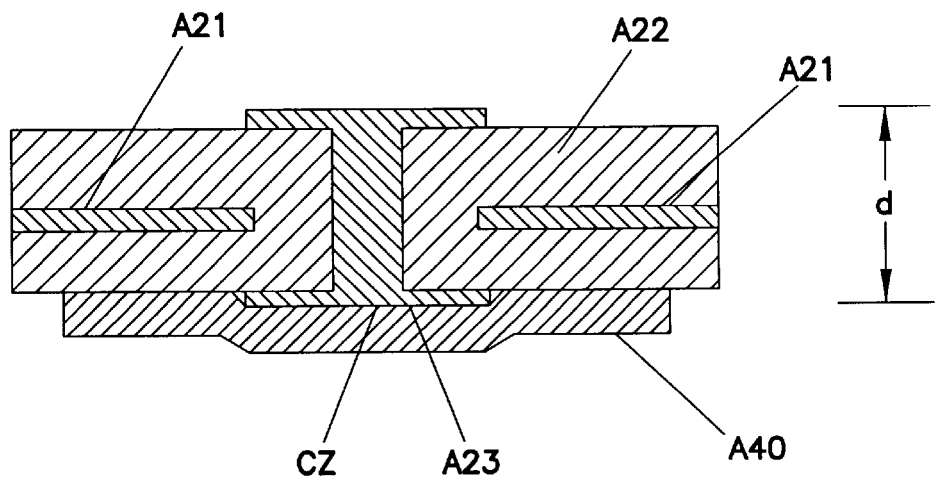
FIGS. 4A–4C show cross-sections of various alternative designs for electrostatic chucks.
Figure 4B:
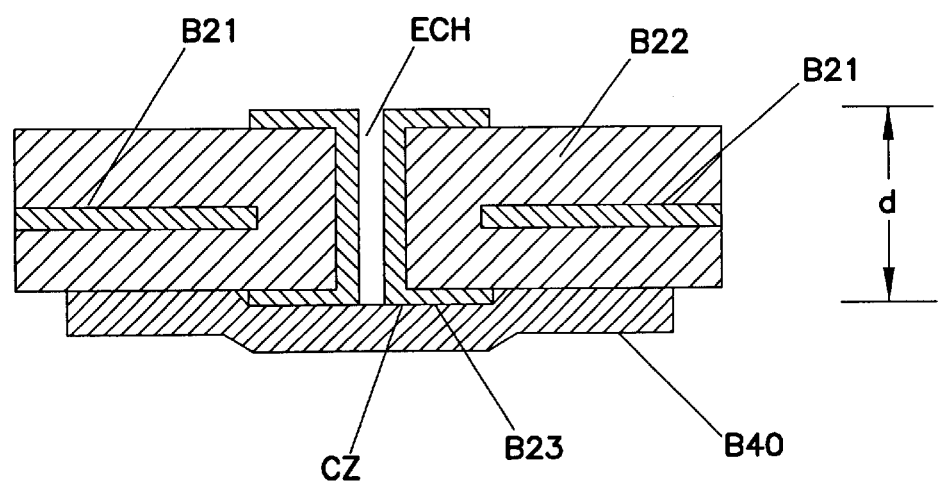
Figure 4C:
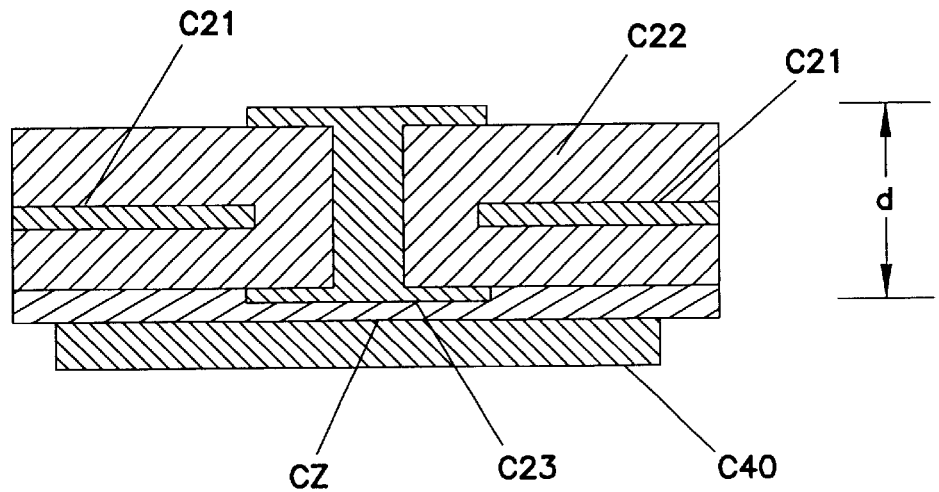

FIGS. 4A–4C illustrate features of electrostatic chucks at a collection zone CZ that can be favorably employed in the invention. In FIG. 4A, the shield electrode A21 (also termed a "ground electrode" based on a preferred bias) is layered within a dielectric A22, which dielectric can be, for example, made of Kaptan® polyimide film (Dupont de Nemours, Wilmington, Del.)(KAPTON® polyimide film can be used as substrate material for Flexible Printed Circuits and can be punched or bonded, etched in alkaline solutions, punched and laser drilled, and can be used to form multilayer polyimide film laminates). The grain-attracting electrode A23 projects out at the surface that attracts the planar substrate A40 (which is, for example, 1 mil thick) and can project out at the opposing side where electrical contacts are formed. The width of the electrostatic chuck d can be, for example, 0.01 inches. As such, the electrostatic chuck can be relatively flexible. In the illustration, the planar substrate wraps over the outwardly projecting grain-attracting electrode A23 in a relatively close-fitting manner. The grain-attracting electrodes typically play a role in adhering the planar substrate. A vacuum chuck used in conjunction with the electrostatic chuck can also contribute to attracting the planar substrate. Tight, smooth adherence of the planar substrate to the electrostatic chuck, which is not disrupted by trapped gas, increases the reliability of grain deposition at the collection zones.

FIG. 4B illustrates an embodiment where the through holes ECH are formed at the grain-attracting electrodes A23.

FIG. 4C illustrates an embodiment where an additional layer of dielectric C22 separates the grain-attracting electrode C23 from the planar substate C40. The electrostatic chuck provided by the configuration of FIG. 4C can be termed a "Pad Indent Chuck" which is useful, for example for depositions of less than about 2 mg, preferably less than about 100 μg, per collection zone CZ (assuming, for example, a collection zone of 3–6 mm diameter, such as 4 mm diameter). The electrostatic chuck provided by the configuration of FIG. 4A can be termed a "Pad Forward Chuck" which is useful, for example for depositions of more than about 20 μg per collection zones CZ (assuming again, a collection zone of 3–6 mm diameter, such as 4 mm diameter), but which is more useful for higher dose depositions than the Pad Indent Chuck.

Planar Substrate Transporter

Figure 5:
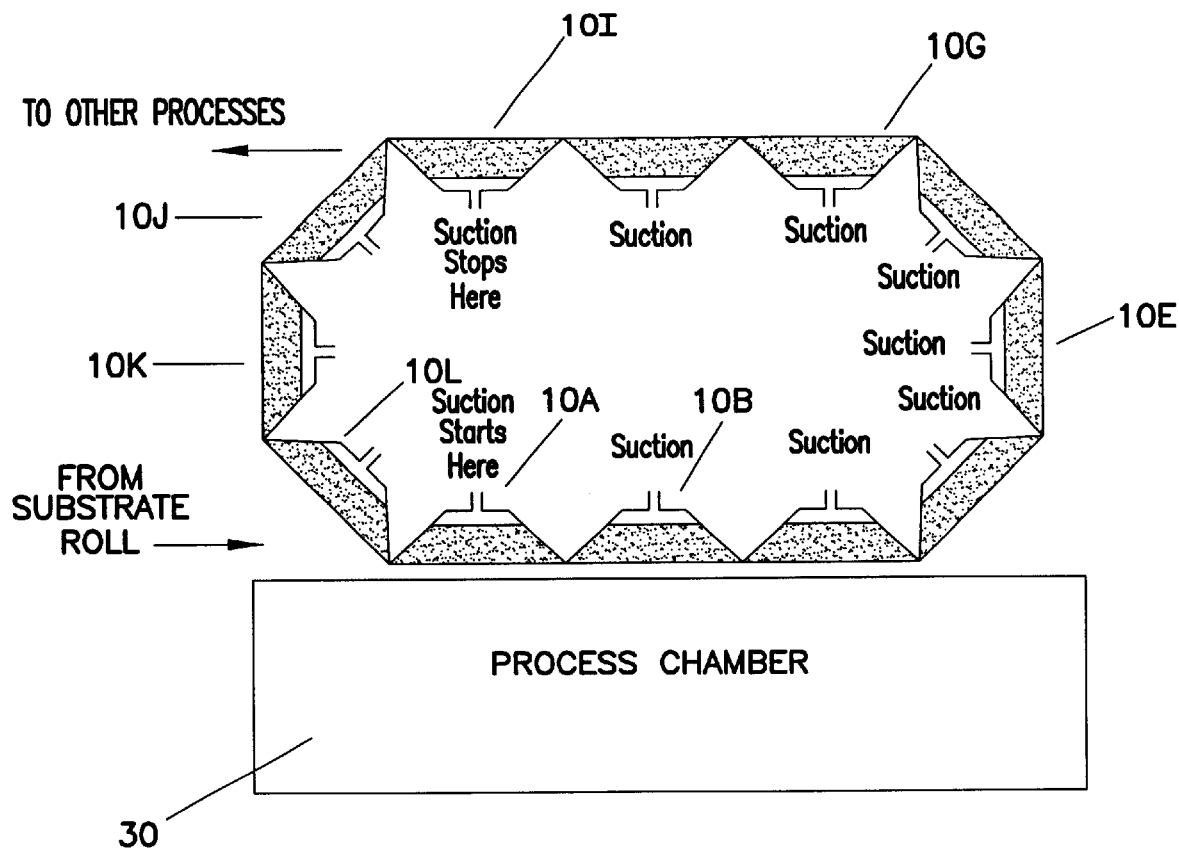
FIG. 5 shows a planar substrate transporter made up of a series of vacuum chucks that define a belt shape.

FIG. 5 shows a planar substrate transporter made up of a series of vacuum chucks 10 that define a belt shape. The rotation of the vacuum chucks 10 around the belt shape can be used to transport a planar substrate through a process chamber 30 at which charged grains are directed at the planar substrate for adhesion mediated by electrostatic chucks positioned on the vacuum chucks 10. The illustrated vacuum chucks 10 rotate around the belt shape, and low pressure is applied to the vacuum chucks as illustrated, allowing suction to be smoothly introduced to a tape (not illustrated) of the planar substrate prior to application of the grains. After application of the grains, the transporter cycles to a point where vacuum is released, allowing the tape of planar substrate to be released and moved to other processes steps. Thus, at time $T_1$, low pressure is applied to vacuum chuck 20A, maintained for vacuum chucks 20B–20H, released for vacuum chuck 20I, and vacuum chucks 20J–20L are maintained at atmospheric pressure. At time $T_2$, which is a time just after that illustrated, low pressure is applied to vacuum chuck 20L, maintained for vacuum chucks 20A–20G, released for vacuum chuck 20H, and vacuum chucks 20I–20K are maintained at atmospheric pressure.

Figure 6:
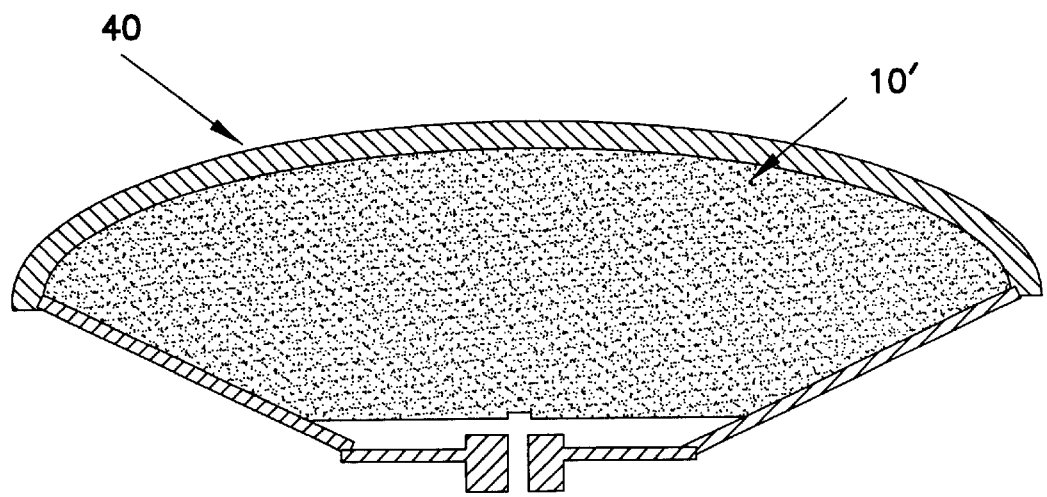
FIG. 6 illustrates a vacuum chuck with a rounded surface.

FIG. 6 illustrates a vacuum chuck 10' with a rounded surface designed to apply a-shape to the planar substrate 40 (e.g., spherical, cylindrical, irregular, indented, and the like). Such shaping of the planar substrate 40 can be useful where the coated planar substrate is usefully shaped for later processing, such as in the formation of gelcaps.

Figure 7:
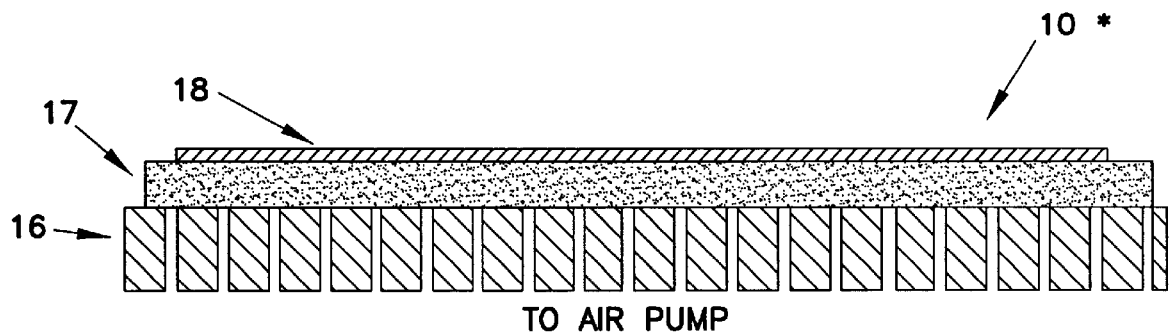
FIG. 7 illustrates a vacuum chuck that utilizes pliable porous materials.

Other, more pliable porous materials can be used in the vacuum chucks used in the invention. A vacuum chuck 10' utilizing such materials is illustrated in FIG. 7, where a rigid or semi-rigid backing plate 16 such as a brass plate with holes or a porous disk as described above is used to support a soft, porous material 17 such as porous Teflon perfluorinated polymer (DuPont de Nemours, Willmington, Del.). The vacuum chuck 10' supports a thin substrate 18.

The planar substrate used with the invention can be any number of materials, but the invention is favorably applied to depositing materials on flexible films such as polyvinylacetate, hydroxypropylmethylcellulose (HPMC), polypropylene, polyester (e.g., Mylar) and polyamide (e.g., nylon) films, which can be plasticized with oils and other known plasticizing agents. One particularly useful embodiment of the invention uses the apparatuses described herein to formulate vehicles for delivering substances to animals, such as vitamins and other bioactive agents, including pharmaceuticals. Accordingly, in many embodiments it is desirable for the planar substrate to be a material suitable for consumption.

Electrostatic and Controlled Field Deposition Methods

In certain electrostatic deposition methods a substrate is sufficiently electrically isolated so that an electrostatic charge can be accumulated on the substrate. One means of accumulating the charge is by taking advantage of the photoelectric effect. In this method the substrate is exposed to ionic bombardment or electromagnetic radiation effective to deposit or strip charges, such as electrons, from the surface of the substrate. Other methods include tribocharging, plasma treatment, induction charging and corona charging. In a more preferred method, an ion emitter is oriented towards the surface on which one intends to create a charge and operated. Such methods of ion printing to controllably electrostatically deposit charged materials such as powders are described in detail in U.S. Pat. Nos. 5,714,007, and 6,007,630 and 6.074.688, which documents are incorporated by reference herein in their entirety.

It should be noted that where the average charge-to-mass ratio of the charged particles of the deposition material is known, the mass of particles that will effectively deposit can be relatively accurately predicted from the amount of charge previously accumulated on the substrate. In particular, for a given type of substrate a calibration database can be compiled. For a given average charge-to-mass ratio of the applied particles, the relationship of accumulated charge to deposited mass can be calibrated for a given set of materials and charging conditions. In a production protocol, the average charge-to-mass ratio of the particles can be monitored, for instance using the velocimeter and a modified quartz crystal monitor described in U.S. Pat. Nos. 5,753,302 and 5,858,099, which documents are incorporated herein by reference in their entirety. The illustrative charge-to-mass monitor functions by applying a voltage to a crystal such as a quartz crystal to establish a vibratory frequency, monitoring changes in the vibratory frequency when exposed to the charged particles, and correlating these changes to the mass of the particles that impact the monitor. Another charge-to-mass monitor uses the cage blowoff method of C. B. Schein and J. Cranch, *J. Applied Phys.* 46: 5140, 1975. With the use of one or more charge-to-mass monitors, feedback loops can be incorporated into the electrical controls of a deposition apparatus. In one preferred embodiment, a charge-to-mass monitor is positioned so as to sample the charge-to-mass of particles at their source (examples for source devices described below) and a charge monitor (for example a device for measuring currents created by the deposition of charged particles) is positioned adjacent to the site of deposition. The sampling values produced at these two sites provide diagnostic data on the operation of the deposition apparatus.

A number of additional methods can be used to monitor the amount of material that is deposited on a solid support or substrate. For example, optical methods can include measuring reflectance, transmission, or fluorescence using laser or non-collimated light of broad or narrow band width. Other sources of directed electromagnetic energy can be used, for instance X-ray absorption or fluorescence or microwave absorption can be used. A tuned circuit can be used to monitor an endpoint at which deposited material creates a resonance with an energy source such as a microwave energy source. Acoustic absorption can also be used, where preferably the sound source is an ultrasound source. Another exemplary measuring method can use a profilameter, which is a laser device that measures the amount the a beam of light is deflected by a surface with deposited material to measure the depth of the deposited material. Further electrical methods can include measuring a capacitance between a conductive material associated with the solid support or substrate (for example a conductive material incorporated into the solid support or a conductive material that has the solid support positioned adjacent to it) and another conductor, where the deposited material is located between the two conductors.

A variety of additional factors can be monitored or controlled to increase the reproducibility of the charge-to-mass ratios generated by the charged deposition material source. For example, controlling the humidity of the local environment, the nature and content of bound solvent in the materials sought to be deposited, the purity of materials sought to be deposited, and the rubbing velocity effected in the tribocharging process can be important.

Another method of attracting charged deposition materials to a surface has been termed "controlled field deposition," and typically involves applying a potential to an electrode which directly or indirectly results in the formation of an attractive electrical field at the surface upon which charged material will be deposited. For example, a substrate can have electrical conductors positioned below the deposition surfaces, and a potential applied to the conductors results in the formation of an attractive field at the surface. Where the separation between the substrate's surface and the conductors is sufficiently small, once an external potential is no longer applied to the conductors the charge of the deposition material results in a charge redistribution in the conductors such that an electrostatic "image" force is formed between the deposition material and the conductors, thereby helping to stabilize the deposition material's adherence to the surface.

Figure 8:
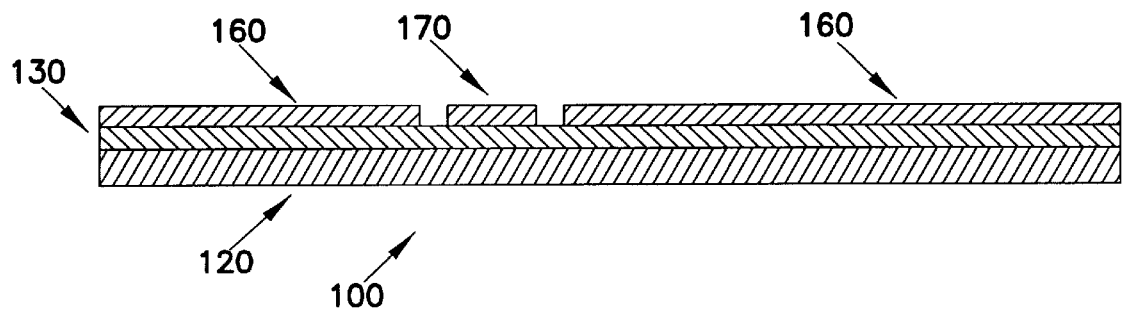
FIG. 8 shows a cross-section of an electrostatic chuck that incorporates a floating electrode.

Further examples of field-generating means include the use of "floating electrodes." A floating electrode is an electrode which develops a localized field as a result of charge redistributions in the floating electrode, which are for example generated by voltages applied across one or more adjacent bias electrodes. Thus, for example, as illustrated in FIG. 8, a floating electrode apparatus 100 can have a backing electrode 120, a non-conductive layer 130, a shielding electrode 160 and a floating electrode 170. In the illustrative floating electrode, a bias potential applied across the backing electrode and the shielding electrode (which two electrodes serve as the bias electrodes) causes a charge redistribution in the floating electrode to create the charged-particle attracting field at the floating electrode. Further description of floating electrodes and other forms of field generating devices for controlled field deposition can be found in U.S. Pat. No. 5,858,099, which document is incorprated herein by reference in its entirety. An advantage of floating electrode devices is that the amount of charged particles that will effectively adhere as a result of the field generated at the floating electrode depends on the size of the bias potential. (For more direct field generating apparatuses, the deposition can in principle continue for as long as a potential is applied.)

The field generating devices for controlled field deposition can be designed (a) to directly apply deposition material onto apparatuses that incorporate electrodes for generating the field or (b) for use with electrostatic chucks (i.e., field application structures) which operate in conjunction with the substrate on which deposition material is to be applied. In the former case (a), it is generally desirable that the metallization processes used to create the electrodes is susceptible to mass production techniques. For example, the metallization can be created by lithographic techniques where finely patterned electrodes are sought or by adhering or fusing metal layers to the substrate. In design (b), the electrostatic chuck is generally effective to electrostatically adhere the substrate to the chuck. This adherence of the substrate to the chuck does not depend on the application of any process for creating a charge on the substrate, but instead is believed to be the result of a redistribution of charges in the substrate in response to the field generated by the electrostatic chuck. Of course, a charge on the substrate can usefully be employed to strengthen electrostatic adherence. A third option is that the substrate is designed to reversibly couple with a device that provides the electrodes, such that the substrate and the coupled device provide a field-generating apparatus. In this way, the electrode structures that can be a source of manufacturing costs remain separate from a consumable on which reagents for conducting a chemical process will be deposited. In addition to the documents recited above, further information on electrode structures and electrostatic chucks can be found in U.S. Pat. No. 5,788,814, which document is incorporated herein by reference in its entirety.

The charge of the particles applied to a substrate can be generated for example by plasma treatment, radiation treatment (including treatment with suitably high energy electromagnetic radiation) or ion bombardment Moreover, the charge can be generated by tribocharging or induction charging (e.g., passing through a tube that is biased to create a field sufficient to induce a charge in grains passing therethrough), wherein two materials with differing triboelectric constants rub against each other and transfer charge between one another. Such methods as tribocharging and induction charging expose the particles to a low amount of reaction-promoting energy, and hence are less susceptible to causing compounds to degrade. Examples of materials that can be used for tribocharging include polytetrafluoroethylene ("TEFLON" polymer) chlorinated propylene, vinyl chloride, chlorinated ether, 4-chlorostyrene, 4-chloro-4-methoxy-styrene, epichlorhydrin, styrene, ethylene, carbonate, ethylene vinyl acetate, methyl methacrylate, vinyl acetate, vinyl butyral, 2-vinyl pyridine styrene, and ethylene oxide; as well as polysulfones and nylons. See, for example, "Triboelectrification of Polymers" in K. C. Frisch and A. Patsis, *Electrical Properties of Polymers* (Technomic Publications, Westport, Conn.), which article is hereby incorporated by reference in its entirety. For example, polytetrafluoroetliylene and polyethylene and will generally adopt a negative charge and create a positive charge on an object rubbed against them. Nylon and other materials will generally adopt a positive charge and create a negative charge on an object rubbed against them. Tribocharging and appliances for dispensing charged particles are describe in U.S. Pat. Nos. 6,007,630 and 5,753,302. U.S. Pat. No. 5,753,302 describes, in particular, an acoustic dispenser that uses vibratory energy and gating electric fields to dispense charged particles for deposition onto the substrate, and is incorporated herein by reference in its entirety.

In some embodiments, the charged particles may be made up in a wet toner wherein particles of liquid material or liquid material with suspended solids are charged. Charging of the liquid particles can be by, for example, tribocharging occurring at the time the particles are formed, utilizing contact potential differences between solid particles and the particles, or modifying the differences in electrical potential using surface treatments such as surfactants. (See, L. B. Schein, *Electrophotography and Development Physics*, Laplacian Press, 1996, p. 227.) Often it is favorable to dry deposit materials to avoid issues of solubility and stability of a chemical. On the other hand, however, liquid phase depositions are often practical, especially where cautionary procedures, such as limiting the time of exposure to the liquid phase and selecting appropriate carrier solvents, are employed. Liquid phase deposition is for example useful where a material to be deposited is not readily converted to a dry form that can be deposited, or where the non-deposited dry form does not retain an activity such as a biological activity.

Several copending applications or issued patents provide information on dry deposition techniques. For example, methods for use of bead transporter chucks and acoustic grain dispensers are set forth in Pletcher et al., "Apparatus for electrostatically depositing a medicament powder upon predefined regions of a substrate," U.S. Pat. No. 5,714,007, issued Feb. 3, 1998; Pletcher et al., "Method and apparatus for electrostatically depositing a medicament powder upon predefined regions of a substrate," U.S. Pat. No. 6,007,630, issued Dec. 28, 1999; Pletcher et al., "Method and apparatus for electrostatically depositing a medicament powder upon predefined regions of a substrate," U.S. Pat. No. 6,074,688, issued Jun. 13, 2000; Pletcher et al., "Apparatus for electrostatically depositing and retaining materials upon a substrate," U.S. Pat. No. 5,669,973, issued Sep. 23, 1997; Datta et al., "Inhaler apparatus with modified surfaces for enhanced release of dry powders," U.S. Pat. No. 5,871,010, issued Feb. 16, 1999; Sun et al., "Acoustic dispenser," U.S. Pat. No. 5,753,302, issued May 19, 1998; Sun et al., "Electrostatic Chucks," U.S. Pat. No. 5,846,595, issued Dec. 18, 1998; Sun et al., "Method of Making Pharmaceutical Using Electrostatic Chuck," U.S. Pat. No. 5,858,099, issued Jan 12, 1999; Sun, "Chucks and Methods for Positioning Multiple Objects on a Substrate," U.S. Pat. No. 5,788,814, issued Aug. 4, 1998; Loewy et al., "Deposited-Reagents for Chemical Processes," U.S. Pat. No. 6,045,753, issued Apr. 4, 2000; Loewy et al., "Solid Support With Attached Molecules," U.S. Pat. No. 6,004,752, issued Dec. 21, 1999; Sun, "Bead Transporter Chucks Using Repulsive Field Guidance," U.S. Pat. No. 6,096,368, issued Aug. 1, 2000; Sun, "Bead manipulating Chucks with Bead Size Selector," U.S. Pat. No. 5,988,432, issued Nov. 23, 1999; Sun, "Focused Acoustic Bead Charger/Dispenser for Bead Manipulating Chucks," U.S. application Ser. No. 09/083,487, filed May 22, 1998. Additional instructional information is found in Sun et al., "AC waveforms biasing for bead manipulating chucks," U.S. Pat. No. 6,149,774, issued Nov. 21, 2000; Poliulak et al., "Dry Powder Deposition Apparatus," U.S. Pat. No. 6,063,194, issued May 16, 2000; and "Pharmaceutical Product and Method of Making," U.S. application Ser. No. 09/095,616, filed Jun. 10, 1998.

In preferred embodiments, a vacuum chuck for positioning objects contains (a) a substrate having multiple open vias, each via permitting air flow; (b) a bottom layer attached to the substrate; (c) a cavity between the bottom layer and the substrate, the cavity permitting air flow between the bottom layer and the substrate; and (d) a pathway for connecting the bottom layer to a vacuum source, wherein each via extends through the substrate to the cavity such that each via is subjected to negative pressure when a vacuum source is applied to the pathway. The bottom layer has a pathway, such as an opening, for the application of negative pressure from a vacuum source through the cavity to the vias, which attracts objects by negative pressure. The term "via", as used herein, is defined as a passageway, and the passageway preferably extends from the top surface of the substrate to the bottom surface of the substrate.

Referring to FIG. 9, for example, the upper layer of the substrate 210 has multiple open vias 220 which are connected to a cavity 230 in the bottom layer 240. The bottom layer of the substrate has an opening 250 for connecting the bottom layer to a vacuum source 260. The beads 270 are held by the chuck 280 using negative pressure applied through the vacuum source 260. The objects can be applied to an electrostatic or vacuum chuck for positioning objects by, for example, pouring them onto the top of the chuck. Alternatively, for example, the objects can be applied using an acoustic dispenser.

One of the conductive layers, such as the lower conductive layer of the electrostatic chuck, can be made x-addressable or x-y-addressable such that the location of the objects attracted to the chuck can be selected. For example, in an x-addressable chuck, the lower conductive layer has rows of openings in which a single row can be activated at one time. Thus, one can select the placement of objects only on a specific row of openings of the electrostatic chuck, rather than on every opening or row or of the chuck. In an x-y-addressable chuck, the area of the lower conductive layer corresponding to each opening or via can be made independent of the remainder of the lower conductive layer corresponding to any of the other openings. Thus, for example, one can select the placement of objects only on specific openings of the electrostatic chuck, rather than on every opening of the chuck.

Thus, in addition to beads, the chucks of the present invention can be used to hold a substrate for application of a pharmaceutically active ingredient. Such substrates include, for example, a suppository, or an edible substrate such as a pharmaceutical tablet, capsule or caplet or a water soluble film such as a hydroxypropyl methyl cellulose resin. Other substrates include dressings, bandages and patches, as well as, for example, a container for an inhaler. For example, the inhaler can be a flat, ceramic disk upon which a plurality of medicament dosages are positioned.

Further, the present invention provides an electrostatic chuck comprising a configuration for depositing a selected number of objects onto a recipient substrate. Preferably, the objects are less than about 3 mm in thickness, and the configuration of the chuck preferably comprises a conductive layer having an x or y-addressable area for depositing a selected number of objects onto the recipient substrate. Preferably, the chuck has multiple areas that are x- or y-addressable, each area preferably corresponding to a separate substrate such as a pharmaceutical carrier. In preferred embodiments, the objects are deposited substantially simultaneously onto multiple substrates, and in certain embodiments, the substrates are connected. For example, the substrates can be a pharmaceutical carrier and the objects can be, for example, particles in a powder, microspheres or liposomes which contain a pharmaceutically active ingredient, and together they create a pharmaceutical dosage form. When the substrates are connected, a multidosage pack can be formed in which the dosage decreases, for example, from one unit to the next, such as with a multidosage pack for birth control. The dosage can be determined by the number of objects placed into each pharmaceutical carrier using an electrostatic chuck. Thus, the present invention provides a multidosage form having units in which each unit has a dosage, at least two units having different dosages, the dosages being determined by the number of micrbspheres in the unit. In certain preferred embodiments, the microspheres are from about I to about 500 microns, in some instances, preferably about 100 to 500 microns, and in other instances, preferably about 50 microns.

Furthermore, a pharmaceutical or other substrate held by an electrostatic chuck, for example, can be coated with a powder, such as a powder having a pharmaceutically active ingredient. Preferably, the powder is in dry micronized form, using for example, an air jet milling process, and the particles are at least about 1 micron in diameter, and preferably from about 1 to about 10 microns, and more preferably about 4 to about 8 microns in diameter. Preferably, the powder is electrostatically charged before application to the chuck, for example, through admixture with beads such as by mechanical shaking. The shaking time is preferably about 30 minutes, and the amount of beads used is preferably calculated so that the surface area of the beads is proportional to the surface area of the particles of the powder. For example, 15 grams of beads can be used with 450 mg of powder.

In further preferred embodiments, electrostatic chucks of the invention are provided for use in charge imaging. For example, a chuck can be used for charge imaging on a substrate to determine the deposition of particles in a particular pattern on the substrate. In preferred embodiments, particles of a powder having a pharmaceutically active ingredient are deposited in a selected pattern onto a pharmaceutical substrate. Preferably, the substrate is a thin dielectric material, such as polypropylene or another thin edible substrate such as hydroxypropyl methyl cellulose, preferably having a thickness of about 25 microns. For example, a plastic substrate for use with an inhaler can be used. In addition to using a thin substrate mechanically attached to the electrostatic chuck, a substrate can be used as a recipient of the particle even when the substrate is not attachable to the electrostatic chuck, since the substrate can be held, for example, by a vacuum chuck that is behind the electrostatic chuck.

The electrostatic chuck with floating electrodes preferably has three layers. The bottom layer is a lower conductive layer, for example silver or copper. Alternatively, for example, the lower conductive layer can be made of a semiconductive material, such as a silicon wafer. The lower conductive layer is optional, but preferred. Without being bound to any particular theory, it is believed that the use of a lower conductive layer prevents charged particles from continuing to deposit indefinitely onto the substrate(s) held by the chuck, and in limiting the amount of particles deposited, may provide for greater uniformity of deposition.

The middle layer is a dielectric layer, such as thermally grown silicon dioxide or polyimide, and is preferably about 0.5 to about 2 mils thick. The top layer is a discontinuous electrode layer with floating and shielding electrodes that are electrically connected, but with a gap between them. The upper conductive layer can be made of, for example, a thin gold film coating, and preferably, the floating and shielding electrodes have the same thickness, which is preferably about 500 nm. In preferred embodiments, the gap between the floating electrode and the shielding electrode is from about 25 microns to about 500 microns. The shape of the floating electrode can be varied, and can be irregular, so long as the gap between the floating electrode and the shielding electrode remains substantially constant. In certain preferred embodiments, the floating electrode is round, and forms a dot that can be used to create a selected pattern. In certain preferred embodiments, the shielding electrode is grounded. The shielding electrode is biased with respect to the lower conductive layer. The polarity of the bias is preferably opposite of the powder to be deposited on the substrate.

Referring to FIG. 10, for example, the chuck 1110 has a lower conductive layer 1120, with a dielectric layer 1130 on top of it. The dielectric layer has an upper conductive layer 1140 on top of it. The upper conductive layer 1140 is electrically connected, but with a gap 1150 between a shielding electrode 1160 and a floating electrode 1170. A top view of the upper conductive layer 1140 is shown in FIG. 11, with the floating electrode 1170 in the center, and a gap 1150 between the floating electrode and the surrounding shielding electrode 1160. The area of the lower conductive layer 1120 corresponding to each floating electrode can be made addressable in rows, like the x-addressable chucking system described above, or individually addressable, like the x-y-addressable chucking system described above.

During use, a bias potential is applied between the shielding electrode and the lower conductive layer. If the particles to be deposited are positively charged, the bias potential will be negative, and if the particles to be deposited are negatively charged, the bias potential will be positive. Preferably, the shielding electrode is connected to ground. During deposition of particles, the length of time of the deposition will preferably be continued until each and every floating electrode has reached its limit in which the potential of the floating electrode matches the potential of the shielding electrode.

Using an electrostatic chuck with floating electrodes to deposit powder onto a substrate, the amount of powder deposited on the substrate is determined by the charge or bias potential of the chuck, and only a finite amount of powder can be deposited. Without being limited to a particular theory, it is believed that the deposition of powder ends when the charges on the floating electrode can no longer be redistributed, which occurs when the shielding electrode and the floating electrode have substantially the same potential. Preferably, both the floating and shielding electrodes will be at ground potential when the deposition is complete. The amount of powder to be deposited can therefore be controlled by controlling the bias potential, and it is unrelated to the duration of deposition, once the limit has been reached. Furthermore, the pattern of deposition is determined by the pattern of the floating electrodes, which creates a charge image.

The invention additionally provides objects having selected areas in which particles are applied to the object via electrostatic means, such as charge imaging. The use of electrostatic means creates a more accurate deposition of particles in a selected image, thus providing for a manner of identification of such an object.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of electrostatically applying grains to a substrate comprising:
   a. adhering the substrate to an electrostatic chuck with a vacuum conveyed to the substrate through the electrostatic;
   b. activating one or more one grain collection zones on the electrostatic chuck by applying voltage to one or more electrodes associated with the grain collection zones;
   c. directing a cloud of grains charged with a given polarity towards the one or more activated grain collection zones, the voltages applied to the associated electrodes selected to attract the grains; and
   d. electrostatically adhering charged grains on portions of the substrate corresponding to the activated grain collection zones.

2. The method of claim 1, wherein the grains are at least 1 micron in diameter.

3. The method of claim 1, wherein the applied voltage selectively attracts charged grains to at least two grain collection zones defined by the electrostatic chuck.

4. The method of claim 1, wherein the grains are 1 to 10 microns in diameter.

5. The method of claim 1, wherein the substrate is a polymeric film.

6. The method of claim 5, wherein the the charged grains comprise a pharmaceutical and the substrate is a flexible polymeric film suitable for consumption by an animal.

* * * * *